US011085931B2

(12) United States Patent
Warthoe

(10) Patent No.: US 11,085,931 B2
(45) Date of Patent: Aug. 10, 2021

(54) UNIVERSAL ASSAY FOR DETERMINING THE QUANTITY OF TNFα INHIBITORY DRUGS AND THEIR CORRESPONDING ANTI-DRUG-ANTIBODIES

(71) Applicant: ATONOMICS A/S, Copenhagen SV (DK)

(72) Inventor: Peter Warthoe, Copenhagen Ø (DK)

(73) Assignee: W. HEALTH L.P., Nassau (BS)

( * ) Notice: Subject to any disclaimer, the term of this patent is extended or adjusted under 35 U.S.C. 154(b) by 415 days.

(21) Appl. No.: 15/541,169

(22) PCT Filed: Jan. 11, 2016

(86) PCT No.: PCT/EP2016/050347
§ 371 (c)(1),
(2) Date: Jun. 30, 2017

(87) PCT Pub. No.: WO2016/110595
PCT Pub. Date: Jul. 14, 2016

(65) Prior Publication Data
US 2018/0003719 A1    Jan. 4, 2018

(30) Foreign Application Priority Data

Jan. 9, 2015  (DK) .......................... PA 2015 70008

(51) Int. Cl.
| G01N 33/68 | (2006.01) |
| G01N 33/542 | (2006.01) |
| G01N 33/543 | (2006.01) |
| G01N 33/564 | (2006.01) |
| G01N 33/58 | (2006.01) |
| G01N 33/94 | (2006.01) |

(52) U.S. Cl.
CPC ....... *G01N 33/6863* (2013.01); *G01N 33/542* (2013.01); *G01N 33/54333* (2013.01); *G01N 33/54393* (2013.01); *G01N 33/564* (2013.01); *G01N 33/581* (2013.01); *G01N 33/582* (2013.01); *G01N 33/585* (2013.01); *G01N 33/6854* (2013.01); *G01N 33/94* (2013.01); *G01N 33/9493* (2013.01); *G01N 2333/525* (2013.01); *G01N 2333/7151* (2013.01)

(58) Field of Classification Search
CPC ............. G01N 33/6863; G01N 33/542; G01N 33/54333; G01N 33/564; G01N 33/581; G01N 33/9493; G01N 2333/7151; G01N 2333/525

See application file for complete search history.

(56) References Cited

U.S. PATENT DOCUMENTS

| 2005/0009050 | A1* | 1/2005 | Nadeau | ................ C12Q 1/6804 |
| | | | | 435/6.18 |
| 2006/0034845 | A1 | 2/2006 | Silence et al. | |
| 2006/0275850 | A1* | 12/2006 | Groome | ................ C07K 16/26 |
| | | | | 435/7.92 |
| 2006/0287317 | A1* | 12/2006 | Smith | ................... C07C 233/60 |
| | | | | 514/237.5 |
| 2008/0008992 | A1* | 1/2008 | Ohshiro | ............. G01N 33/5306 |
| | | | | 435/5 |
| 2011/0097723 | A1* | 4/2011 | Liu | ...................... C12Q 1/6816 |
| | | | | 435/6.1 |
| 2012/0329172 | A1 | 12/2012 | Singh et al. | |
| 2013/0203075 | A1 | 8/2013 | Svenson et al. | |
| 2013/0295685 | A1 | 11/2013 | Singh et al. | |
| 2014/0045276 | A1 | 2/2014 | Singh et al. | |

FOREIGN PATENT DOCUMENTS

| EP | 2281631 | 2/2011 | |
| JP | 2005077301 | 3/2005 | |
| WO | 02/18950 | 7/2002 | |
| WO | 2008/006588 | 1/2008 | |
| WO | 2014 083520 | 7/2014 | |
| WO | WO-2015128548 A1 * | 9/2015 | ......... G01N 33/6857 |
| WO | 2016/097400 | 6/2016 | |
| WO | 2016/110595 | 7/2016 | |

OTHER PUBLICATIONS

Eglen et al. (Current Chemical Genomics 2008 vol. 1, p. 2-10). (Year: 2008).*
Leister et al. (Current Chemical Genomics 2011 (Year: 2011).*
Svenson et al. (Rheumatology 2007 vol. 46, p. (Year: 2007).*
TechNote 2013 (Year: 2013).*
Lumigen (2013 Lab Protocol). (Year: 2013).*
Steenholdt et al. (Gastroenterology & Hepatology 2012 vol. 8, p. 131-134) (Year: 2012).*
JP 200507730 application English Translation Inventors: Mariko et al. (Year: 2005).*
Aarden, Lucien, Sigrid R. Ruuls, and Gertjan Wolbink. "Immunogenicity of anti-tumor necrosis factor antibodies—toward improved methods of anti-antibody measurement." Current opinion in immunology 20.4 (2008): 431-435.
Bendtzen, Klaus. "Anti-TNF-α biotherapies: perspectives for evidence-based personalized medicine." (2012).

(Continued)

*Primary Examiner* — Changhwa J Cheu
(74) *Attorney, Agent, or Firm* — Duane Morris LLP; Gregory M. Lefkowitz; Brandon A. Chan

(57) ABSTRACT

The present invention relates to a kit of parts and methods for determining the presence and quantity of one or more TNF-α inhibitor drugs and/or anti-TNF-α inhibitor drug antibodies in one or more biological samples each comprising less than 200 μl, the method comprising the steps of providing a reaction liquid comprising the sample, a first TNF-α conjugate comprising TNF-α and a first conjugated moiety and a second TNF-α conjugate comprising TNF-α and a second conjugated moiety, said second moiety being capable of generating or ameliorating a detectable signal in the presence of a molecular complex comprising a TNF-α inhibitor, followed by detecting the change in signal when the complex between the TNF-α inhibitor drug, the first TNF-α conjugate and a the second TNF-α conjugate forms.

7 Claims, No Drawings

(56) References Cited

OTHER PUBLICATIONS

Bendtzen, Klaus, and Morten Svenson. "Enzyme Immunoassays and Radioimmunoassays for Quantification of Anti-TNF Biopharmaceuticals and Anti-Drug Antibodies." Detection and Quantification of Antibodies to Biopharmaceuticals: Practical and Applied Considerations (2011): 81-101.
Bendtzen Klaus et al: "Individualized monitoring of drug bioavailability and immunogenicity in rheumatoid arthritis patients treated with the tumor necrosis factor alpha inhibitor infliximab", Arthritis & Rheumatism, vol. 54, No. 12, Dec. 2006 (Dec. 1, 2006), pp. 3782-3789, XP002626408, ISSN: 0004-3591.
Casper Steenholdt and Klaus Bendtzen. "Antibodies Against "Human" Biopharmaceuticals: Individualized Therapy with TNF-alpha Inhibitors Guided by Immunopharmacologic Assessments." Autoantibodies—(Third Edition)—(2014), Chapter 93, pp. 803-816, Elsevier B.V. ISBN: 978-0-444-56378-1.
Kelley et al., "Theoretical Considerations and Practical Approaches to Address the Effect of Anti-drug Antibody (ADA) on Quantification of Biotherapeutics in Circulation", AAPS Journal, vol. 15, No. 3, Jul. 2013 (Jul. 2013), p. 646-658.
Lee, "ADME of monoclonal antibody biotherapeutics: knowledge gaps and emerging tools", Bioanalysis, vol. 5, No. 16, Aug. 1, 2013 (Aug. 1, 2013), p. 2003-2014.
Koskinen et al., "A novel separation-free assay technique for serum antibodies using antibody bridging assay principle and two-photon excitation fluorometry", Feb. 20, 2006 (Feb. 20, 2006), vol. 309, No. 1-2, p. 11-24.

\* cited by examiner

UNIVERSAL ASSAY FOR DETERMINING THE QUANTITY OF TNFα INHIBITORY DRUGS AND THEIR CORRESPONDING ANTI-DRUG-ANTIBODIES

CROSS-REFERENCE TO RELATED APPLICATIONS

This application is a §371 national stage entry of International Application No. PCT/EP2016/050347, filed Jan. 11, 2016, which claims priority to Danish Patent Application PA 2015 70008, filed Jan. 9, 2015, the entire contents of which are incorporated herein by reference.

FIELD OF THE INVENTION

The present invention relates to the monitoring or assaying of biological samples for the presence or absence of TNF alpha inhibitor drugs and their antibodies, such as anti-drug antibodies (ADA), in patients who may have developed an antibody response in treatments with TNF alpha inhibitor drugs.

Accordingly, in one embodiment, the present invention relates to a method for determining the quantity of a TNF alpha inhibitor drug in a biological sample, preferably a blood sample, comprising less than 200 µl.

In a further embodiment, the present invention relates to a method for determining the quantity of one or more anti-drug antibodies (ADAs) against a TNF alpha inhibitor drug in a biological (blood) sample comprising less than 200 µl.

In a further embodiment, the present invention relates to a method for determining the quantity of TNF alpha inhibitor drugs and their antibodies in a biological (blood) sample comprising less than 200 µl.

Further, the invention relates to a kit of parts for determining the quantity of TNF alpha inhibitor drugs and their antibodies in a biological sample.

BACKGROUND OF THE INVENTION

Anti-tumor necrosis factor (TNF) therapy has become important for use in the management of several chronic immunoinflammatory diseases. Three recombinant anti-TNF alpha drugs are currently approved for clinical use in patients with various chronic inflammatory diseases such as rheumatoid arthritis (RA), Crohn's diseases and severe psoriasis: 1) Remicade™ (infliximab), a mouse-human IgG1-kappa anti-TNF-alpha monoclonal antibody, 2) Enbrel™ (etanercept), a fusion protein of human TNF receptor 2 and human IgG1, and 3) Humira™ (adalimumab), a fully human IgG1-kappa anti-TNF-alpha monoclonal antibody. Two other anti-TNF-alpha antibody constructs have shown promise in pivotal phase III trials in patients with some of the same diseases: 4) Cimzia™ CDP870 (certolizumab pegol), a PEGylated Fab fragment of a humanized anti-TNF-alpha monoclonal antibody, and 5) CNTO 148 (golimumab), a fully human IgG1-kappa anti-TNF-alpha monoclonal antibody. All of these proteins dramatically lower disease activity and, in some patients, may induce remission.

Unfortunately, however, not all patients respond favorably to anti-TNF alpha drugs. Some patients either do not respond at all (primary response failure) or they respond initially but have later relapses (secondary response failure) despite increased dosage and/or more frequent administration of the drugs. The reason(s) for these response failures are not always clear but interindividual and even intraindividual differences in bioavailability and pharmacokinetics may contribute to the problem. Immunogenicity of the drugs causing patients to develop anti-antibodies is a problem now recognized by many investigators, drug-controlling agencies, health insurance companies and drug manufacturers. Monitoring of patients for circulating levels of functional anti-TNF alpha drugs and anti-antibody development is therefore warranted so that administration can be tailored to the individual patient and so that prolonged therapies can be provided effectively and economically with little or no risk to the patients.

Following repeated infusions, the formation of neutralizing anti-TNF alpha drugs becomes a problem requiring increased doses or more frequent drug administration and may necessitate discontinuation of therapy because of secondary response failure and/or infusion-related side effects; this has been observed in both RA patients and in patients with other immunoinflammatory diseases. In clinical practice, however, patients with RA or any other chronic inflammatory disease treated with infliximab may differ considerably from the average patient in randomized clinical trials. For example, even though the initial bioavailability of infliximab approaches 100% because of the intravenous administration of the drug, differences in pharmacokinetics may result in individual patients having inadequate drug levels for extended periods of time between infusions. This problem can be exaggerated by the appearance of antibodies. A number of studies have reported a concentration-effect relationship of therapeutic proteins directed against TNF-alpha in patients with RA and Crohn's disease and an inverse relation between drug levels and ADA.

Indeed, response failure due to induction of antibodies (ADAs) against biopharmaceuticals (in particular TNF alpha inhibitor drugs) is increasingly being realized. Development of host (patient) antibodies against biopharmaceuticals is particularly relevant when the drug is delivered chronically, i.e. periodic administration over a period of months or years. Anti-TNF alpha drugs are typically delivered chronically. When measuring ADAs, it is of importance is to identify the neutralizing ADAs from the non-neutralizing ADAs.

The development of host antibodies can be remedied by increasing dosage although this is typically a delayed and rather temporary response as the prescription dosage is typically only increased once patient symptoms noticeably deteriorate, and the increased dosage may well result in further augmentation of the patients' immune system. Typically, the more preferred remedy is to switch treatment regime and to use another TNF alpha inhibitor drugs.

Accordingly, correctly assessing the quantity of Anti-TNF alpha drugs (TNF alpha inhibitor drugs) and their antibodies (ADAs) in biological samples from patients poses ubiquitous challenges to medicinal practioneers.

Different methods have been used to assess circulating levels of TNF alpha inhibitor drugs and their anti-drug-antibodies. Some of these are based on enzyme immunoassays (EIA) where the TNF alpha inhibitor drugs are immobilized on plastic beads or wells and bridging the binding of labeled TNF alpha inhibitor drugs by anti-drug-antibodies is used as readout. Other assays detect complexes of anti-drug-antibodies and TNF alpha inhibitor drugs by selective absorption for example by the binding of Fab of an immunoglobuline TNF alpha inhibitor to protein A, or to antibodies to anti-light chain Fab.

These methods, however, are cumbersome and specific towards a given TNF alpha inhibitor drugs (the method cannot be universally applied with function towards several different TNF alpha inhibitor drugs). Further, these methods may not be suitable for the detection and quantification of both TNF alpha inhibitor drugs and their antibodies in the same assay procedure.

Thus, the development of assays that can be used to monitor bioavailability of several TNF alpha inhibitor drugs and antibody development against several TNF alpha inhibitor drugs is of direct clinical importance.

Accordingly, there is a constant need in the art for alternative methods for determining TNF alpha inhibitor drugs and their antibodies, especially methods that are universally applicable and provide increased accuracy and give increased reproducibility.

It is an object of the invention to provide such methods and kits of parts for use in the methods.

In particular, there is a need in the art for kits of parts and methods which can be applied universally, in the sense that the medical practioneer can assess different individual patients (patients potentially using different prescription medicaments) using the same assay. It is an object of the invention to provide such methods and kits of parts.

Measurements of analytes in blood samples by patient- and user-friendly equipment conventionally aim at analysing blood samples consisting of less than 200 µl blood. Such quantities are easily obtained by the individual patients without being associated with serious health risks.

Thus, there is a need in the art for methods and devices capable of analysing TNF alpha inhibitor drugs and their antibodies quantities in blood samples comprising less than 200 µl blood. Even more specifically, there is a need in the art for methods and devices capable of analysing TNF alpha inhibitor drugs and their antibodies quantities in blood samples comprising less than 180 µl blood, such as less than 150 µl, such as less than 100 µl, such as less than 50 µl, such as less than 20 µl, such as less than 10 µl, such as less than 9 µl, such as less than 8 µl, such as less than 7 µl, such as less than 6 µl, such as less than 5 µl, such as less than 4 µl, such as less than 3 µl, such as 2 µl or less blood. It is an object of the invention to provide such methods.

Another challenge is to increase the ease of each analysis, preferably to a level at which measurements of TNF alpha inhibitor drugs and their antibodies in blood can be made by the patient without the assistance of medicinal practioneers. Further, it is also a challenge to bring down the costs to a level at which each measurement is affordable by the consumer.

Accordingly, there is a need in the art for methods and patient-friendly kits of parts allowing for accurately and easily measuring the level of TNF alpha inhibitor drugs and their antibodies in blood samples. Further, there is a need in the art for methods and kits of parts that allow for a simple and easy handling of samples and blood analysis. It is an object of the invention to provide such methods.

DESCRIPTION OF THE INVENTION

As stated above, there is a ubiquitous need in the art for methods and patient-friendly kits of parts providing accurate, sensitive and reproducible measurements of the level of (multiple) TNF alpha inhibitor drugs and their antibodies in biological samples. In some embodiments, the biological sample according to the invention is selected from the group consisting of blood, blood serum, lymph fluid, lymph node tissue, spleen tissue, bone marrow, or an immunoglobulin enriched fraction derived from one or more of these tissues.

According to the present invention, a blood sample means a sample of full blood from a patient or a material derived therefrom (such as serum).

The above objects of the invention have been solved according to the present invention, which provides a highly effective and sensitive assay for detection of the level of TNF alpha inhibitor drugs and their antibodies in (blood) samples.

The basic principle of the assay is the use of "labled" TNF alpha as the universal ligand specific to the TNF alpha inhibitor drugs. The universal ligand is tabled in the sense that it forms a molecular complex in the presence of the TNF-α inhibitor drug, which complex is capable of generating or ameliorating a detectable signal.

Thus, in a first embodiment, the invention provides a method for determining the presence and quantity of one or more different TNF-α inhibitors in one or more blood samples each comprising less than 200 µl, the method comprising the steps of:
  a. providing a first TNF-α conjugate comprising TNF-α and a first conjugated moiety,
  b. providing a second TNF-α conjugate comprising TNF-α and a second conjugated moiety, said second moiety being capable of generating or ameliorating a detectable signal in the presence of a molecular complex comprising a TNF-α inhibitor, the first TNF-α conjugate and the second TNF-α conjugate,
  c. providing a reaction liquid comprising the first and the second TNF-α conjugates and contacting the sample with the reaction liquid, whereby a detection liquid comprising the sample potentially comprising the TNF-α inhibitor and the first and the second TNF-α conjugates, is formed,
  d. detecting the change in signal following step c, (when the complex comprising the TNF-α inhibitor and the first and the second TNF-α conjugates is formed), and
  e. determining the quantity of the TNF-α inhibitor by comparing the obtained results with an internal standard.

The internal standard may be provided by a preproduced standard curve which plots the signal produced by the above method performed on a corresponding sample having a known (spiked) content of each particular TNF-α inhibitor drug. The assay performs differently for different TNF-α inhibitor drugs due to differences in binding affinity necessitating different internal standards for different TNF-α inhibitor drugs.

In one embodiment of the invention, the level of haemoglobin is also measured and used to assess the relative level of TNF alpha inhibitor drugs and their antibodies in the blood sample.

The First and the Second TNF-α Conjugates

The TNF-alpha conjugates (the first and the second) according to the invention may in some embodiments be identical and in other embodiments function pairwise.

In a highly preferred embodiment, the TNF-alpha conjugates are solid particles coated with TNF alpha. In these embodiments, the first and the second moieties are solid particles and the detectable signal provided by the formation of the complex comprising the TNF-α inhibitor and the first and the second TNF-α conjugates may for example be a change in turbidity of the reaction liquid and the detection liquid. It was surprisingly observed that in such embodiments, a single TNF-α inhibitor drug was capable of binding and immobilising more than one of the TNF-alpha conjugates (particles), thereby producing a detectable mesh proportional to the concentration of drug.

However, and in particular with respect to the TNF-α inhibitor Enbrel, it was found that the addition of a further ligand, a TNF alpha inhibitor-binding agent, binding individual TNF-α inhibitors together (at sites other than the binding site for TNF-alpha) increased the assay performance drastically. As an example of such a TNF alpha inhibitor-binding agent (see below example 1), polyclonal rabbit anti-Human IgG Fc is added, which bind the individual TNF-alpha inhibitor molecules together at sites other than the binding site for TNF-alpha.

Accordingly, in a highly preferred embodiment, the method of the invention comprises the further addition to the reaction liquid of a TNF alpha inhibitor-binding agent capable of binding individual TNF-alpha inhibitor molecules together. Preferably, such an additional ligand is a polyclonal anti-TNF-alpha inhibitor antibody, or an antibody directed at regions of the TNF-alpha inhibitor molecules that does not interact in the binding to TNF alpha. As a TNF alpha inhibitor-binding agent, any compound or protein (preferably an antibody) may be used that more or less specifically binds to two or more TNF-alpha inhibitors but does not interact in the binding to TNF alpha. The TNF alpha inhibitor-binding agent may be selected from the list consisting of anti-Ig, such as Fc-specific or Fab-specific antibodies, protein G, Protein A, Protein H, Protein L, and Protein A/G fusion protein. Accordingly, the TNF alpha inhibitor-binding agent may be selected to specifically bind the particular subtype of the TNF alpha inhibitor, such as when using Protein A to bind with high affinity to human IgG1 and IgG2.

It is to be understood that the TNF alpha inhibitor-binding agent is not usually intended to be specific to particular TNF alpha inhibitor. Usually, the TNF alpha inhibitor-binding agent will bind different antibodies with different specificities within the same or different classes or subtypes of antibodies.

In a highly preferred embodiment of the invention, the first and the second moieties are both solid particles of identical or different sizes, such as polystyrene particles, latex particles, sepharose or agarose beads or beads of other polysaccharide polymers, or magnetic or paramagnetic beads. Further, in a highly preferred embodiment, when the first and the second moieties are moieties that do not function in pairs, i.e. are both solid particles, a TNF alpha inhibitor-binding agent capable of ligating one TNF-α inhibitor with another TNF-α inhibitor, is preferably used.

In another preferred embodiment of the invention, the TNF-alpha conjugates comprise a first and a second conjugate functioning in a pair. Such pairs are for example a first TNF alpha conjugate comprising TNF alpha conjugated to an enzyme and a second TNF alpha conjugate comprising TNF alpha conjugated to a substrate for the enzyme. Accordingly, in a preferred embodiment of the invention, the first moiety is an enzyme and the second moiety a substrate for the first moiety. As a preferred example of such system is the horseradish peroxidase (HRP) system.

In another preferred embodiment of the invention, such pairs are for example a first TNF alpha conjugate comprising TNF alpha conjugated to a fluorophore and a second TNF alpha conjugate comprising TNF alpha conjugated to a modulator of the fluorophore (such as a quencher). Accordingly, in a preferred embodiment of the invention, the first moiety is a fluorophore and the second moiety is a modulator of the fluorescence provided by the first moiety. As preferred examples of such systems are homogeneous antibody-based proximity extension assays such as is the fluorescence based Alpha screen from Perkin Elmer or the chemiluminescence based SPARCL (Spatial Proximity Analyte Reagent Capture Luminescence) technology from Beckman Coulter.

According to the present invention, fluorophore means an agent or means, the presence of which in the reaction and detection liquid causes the emission of detectable electromagnetic radiation (light), such as a photoluminescent or chemiluminescent marker compound. In a preferred embodiment, the fluorophore is an agent that emits detectable light in response to being contacted or irradiated with light of a different wavelength.

Spiking Assay

It was surprisingly found possible to validate the measurement of the amount of TNF-α inhibitor measured by the method according to the invention (by detecting the presence/absence of patient-derived anti-drug-antibodies), and/or to detect and quantify the level of patient-derived anti-drug-antibodies in the sample in the same assay by use of an indirect measurement, where samples are spiked with a known amount of the respective TNF-α inhibitor.

By comparing an obtained measurement with the expected result of such measurement (comprising a spiked amount of TNF alpha drug) the presence/absence of anti-drug-antibodies in the sample could be established. If such are present, the measured amount of TNF-α inhibitor should be less than the expected amount in the spiked sample.

By comparing more than one obtained measurement with the corresponding expected results of such measurement, the quantity of anti-drug-antibodies in the sample can be established (see example 2 below).

Thus, in a highly preferred embodiment, the method according to the invention comprises the additional step of spiking the sample or the reaction liquid with one or more known amounts of a TNF-α inhibitor prior to the detection performed in step d., thereby providing a method for determining the validity of the measurement of the presence of the TNF-α inhibitor in the sample, and further providing a method for the determination of the presence and quantity of one or more different TNF-α inhibitor antibodies in the sample.

The term anti-TNF alpha inhibitor drug-antibodies (ADA) as used herein refers to a plurality of antibodies derived from a biological sample of a subject that specifically recognise a particular TNF alpha inhibitor drug. It may be a plurality of antibodies within the same class or isotypes of antibodies, such IgG, IgE, IgA, IgD, and IgM. Accordingly, in some embodiments the ADAs being detected or measured are within a particular isotype of antibodies, such as IgG and/or IgE. Typically the specific antibodies of the biological sample have not been purified with respect to any specific component, such as specific antibodies of the biological sample. Measurement of the amount of ADA herein refers to the determination of the concentration of host-derived antibody against the TNF alpha inhibitor drug in the subject (such as in the sample, or tissue corresponding to the sample).

Thus, the invention also relates to a method for determining the presence and quantity of one or more different TNF-α inhibitor drug antibodies (ADAs) in one or more blood samples each comprising less than 200 μl, the method comprising the steps of:

a. providing a first TNF-α conjugate comprising TNF-α and a first conjugated moiety, b. providing a second TNF-α conjugate comprising TNF-α and a second conjugated moiety, said second moiety being capable of generating or ameliorating a detectable signal in the presence of a molecular complex comprising a TNF-α inhibitor, the first TNF-α conjugate and the second TNF-α conjugate,
c. providing a reaction liquid comprising the first and the second TNF-α conjugates, a spike containing a known amount of the TNF-α inhibitor, and contacting the sample with the reaction liquid, whereby a detection liquid comprising the sample (potentially comprising the TNF-α inhibitor drug antibody), the spike amount of the TNF-α inhibitor and the first and the second TNF-α conjugates, is formed (the spike amount of TNF-α inhibitor drug may be added to the sample or to the reaction liquid),
d. detecting the change in signal following step c, (when the complex comprising the TNF-α inhibitor and the first and the second TNF-α conjugates, is formed), and
e. determining the quantity of the TNF-α inhibitor by comparing the obtained results with an internal standard,
f. determining the presence or absence of the TNF-α inhibitor anti-body by comparing the obtained results with an internal standard such that a change in signal that is less than would be expected following the addition of sample and spike to the reaction liquid indicates the presence of TNF-α inhibitor antibodies.

In a preferred embodiment, at least one repeat of the steps a-f is performed with a second spike of a known amount of the TNF-α inhibitor drug, or alternatively comprising the additional steps g and h of providing a second spike of a known amount of the TNF-α inhibitor, adding the second spike to the detection liquid following step d, and, subsequently detecting the change in signal provided by the addition of the second spike, and determining the quantity of TNF-α inhibitor antibodies in the sample.

Since the method according to the invention can be performed universally on different types of TNF alpha inhibitor drugs, the method according to the present invention is highly suited for the provision of a universal assay applicable directly in the clinic for the measurement of levels of prescribed medicaments (drugs) in individual patients.

Accordingly, in a preferred embodiment of the invention, the TNF-α inhibitor is a prescription medicament. Presently preferred prescription medicaments are selected among etanercept (Enbrel), infliximab (Remicade), adalimumab (Humira), certolizumab pegol (Cimzia), and golimumab (Simponi).

In one embodiment, the invention is a kit of parts for determining the quantity of a TNF-α inhibitor in a sample and/or for determining the quantity of a TNF-α inhibitor antibody in a sample, the kit of parts comprising:
a. a first TNF-α conjugate comprising TNF-α and a first conjugated moiety as defined above,
b. a second TNF-α conjugate comprising TNF-α and a second conjugated moiety as defined above,
c. one or more spike standard solutions each comprising a known amount of a TNF-α inhibitor drug.

Preferred devices for the detection measurements according to the present invention are devices capable of detecting the signal produced or ameliorated in a 200 µl or less sample detection liquid. Such devices include e.g. for example the Atolyzer® and similar devices such as devices according to e.g. EP2281631 and related applications in the name of Atonomics A/S.

Preferably, the kit of parts comprises a standard solution (spiking solution) of more than one TNF-α inhibitor, such as preferably at least two different spike standard solutions comprising at least two different TNF-α inhibitors. In a preferred embodiment the kit of parts comprises at least three, such as at least four, different spike standard solutions comprising at least three, such as at least four, different TNF-α inhibitor drugs. Preferably, the kit of parts according to the invention comprises a standard spike solution of at least two of the TNF-α inhibitors etanercept (Enbrel), infliximab (Remicade), adalimumab (Humira), certolizumab pegol (Cimzia), and golimumab (Simponi).

In a highly preferred embodiment of the invention the kit of parts comprises at least one standard spike solution of the TNF-α inhibitor etanercept (Enbrel).

In a preferred embodiment, the kit of parts also comprise a TNF alpha inhibitor-binding agent, i.e. a ligand capable of binding individual TNF-α inhibitors together. Preferably, such an additional ligand is a polyclonal anti-TNF-alpha inhibitor antibody, or an antibody directed at regions of the TNF-alpha inhibitor molecules that does not interact in the binding to TNF alpha.

When measuring ADAs it is of importance is to identify the neutralizing ADAs from the non-neutralizing ADAs. Combining the patients' non-responder profile with the spike recovery method described in this patent application makes it possible to propose a treatment regime for patients with insufficient clinical response to particular anti-TNF alpha drugs.

The assay according to the present invention may also include measurement of the IgG4 antibodies in the pool of potential neutralizing ADAs. Detecting IgG4 antibodies has always been a challenges for the "bridge"-based ELISA assays since IgG4 antibodies are monovalent.

In another embodiment, the present invention relates to a method of treatment of a disease in a patient being treated with a TNF-α inhibitor drug, said method comprising performing the method according to the invention on a sample derived from the patient to determine whether the patient requires either an altered dosage regime of the TNF-α inhibitor drug or an alternative TNF-α inhibitor drug or an alternative pharmaceutical therapy.

The method according to the invention may also be used for identifying primary non- or low-responders for a particular TNF alpha treatment. These may, for example, be patients that happen to have an innate or a pre-developed immunoglobulin response to the TNF alpha inhibitor.

Thus, in another embodiment, the present invention relates to a method of identifying the optimal TNF-α inhibitor drug treatment of a disease in a patient, said method comprising performing the method according to the invention on a sample derived from the patient to determine whether the patient requires either an altered dosage regime of the TNF-α inhibitor drug or an alternative TNF-α inhibitor drug or an alternative pharmaceutical therapy.

The method according to the invention may also, for example, be used for identifying patients with secondary response failure. Secondary response failures can be asymptomatic, i.e. the only symptoms are that the treatment has become less effective or even non-effective. In this instance, the use of the method according to the invention can be used to identify the development of secondary response failure before the patient or the medical practitioner has noticed that the treatment is less effective. A higher dosage of treatment may be applied to ensure that the correct and effective in vivo concentration is achieved, or alternative treatments can be selected, or a combination thereof.

Accordingly, the invention comprises a method of determining whether the lack of treatment response in a patient is due to the formation of patient-derived antibodies against the TNF alpha inhibitor. The invention thus provides for a method of selecting the appropriate drug treatment for a patient suffering from a disease which is treatable with a TNF alpha inhibitor (using the method steps referred to herein).

EXAMPLES

Assay Principle

TNFα (human) is immobilized onto carboxylated polystyrene particles (R1). The TNF-alpha inhibitor drug binds to the TNFα coated particles and facilitates particle agglutination. To enhance the particle agglutination reaction (in response to the presence of TF alpha inhibitor drugs), a polyclonal rabbit anti-Human IgG Fc is added (R2) which interacts with the TNF-alpha inhibitor molecules.

Reagent 1: HEPES pH 7.2 10 mmol/L Polyethylenglycol (PEG), NaCl, human TNFα molecules bound to carboxylated polystyrene particles, detergents and stabilizers.

Reagent 2: Borate buffer 4.6 mmol/L. Polyclonal polyclonal rabbit anti-Human IgG Fc, polyethylenglycol (PEG), NaCl, detergents and stabilizers.

Example 1. The TNFα Inhibitory Universal Drug Assay Procedure

The objective of example 1 was to investigate if different TNFα drugs (Enbrel and Humira) could be measured using the developed assay principle (in the embodiment of particle enhanced immunoturbidimetric measurements) having an identical affinity ligand (TNFα) attached to the particles in separate assays (Enbrel array and Humira assay).

Samples

Etanercept was spiked in human plasma which did not contain any kind of drug or anti-drug antibodies and was measured using the particle-enhanced immunoturbidimetric method. The data are shown in Table 1.

Adalimumab (Humira) was spiked in human plasma which did not contain any kind of drug or anti-drug antibodies and was measured using the particle-enhanced immunoturbidimetric method. The data are shown in Table 1.

Assay Principle
Assay

The sample containing the TNF-alpha inhibitor was added to a reaction liquid containing reagent 1. Reagent 2 was added to the reaction and the development in the absorbance at 570 nm was measured.

TABLE 1

Adalimumab and Etanercept are measured using the particle-enhanced immunoturbidimetric method.

| Drug concentration (μg/mL) spiked in human plasma. | Adalimumab Absorbance (570 nm) | Etanercept Absorbance (570 nm) |
|---|---|---|
| 0 | 0.000227 | 0.000827 |
| 0 | 0.000214 | 0.000695 |
| 0 | 0.000251 | 0.000751 |
| 1.0 | 0.0489 | 0.0255 |
| 1.0 | 0.0476 | 0.0243 |
| 1.0 | 0.0463 | 0.0236 |
| 5.0 | 0.188 | 0.0961 |
| 5.0 | 0.191 | 0.0968 |
| 5.0 | 0.195 | 0.0977 |
| 10.0 | 0.394 | 0.201 |
| 10.0 | 0.397 | 0.211 |
| 10.0 | 0.386 | 0.203 |

As seen in Table 1 and each of the two TNFα-inhibiting anti-inflammatory drugs generates different signals at different concentrations in the immunoturbidimetric assay setup which is most likely due to different affinities towards the TNFα molecule immobilized on the polystyrene particles.

This example shows that accurate measurements of the concentration of different TNF-alpha inhibitors in human samples (free of anti-drug-antibodies) are possible by use of the described method.

Example 2. Measuring the Presence of Anti-Drug-Antibodies (ADAs)

The objective of example 2 was to investigate if the method can be used to detect the presence of ADAs.

Spike and recovery can be used for validating the analytical validity of immunoassays. If there are no other species of binders competing for the analyte, and a known amount of analyte is added to a human blood, serum or plasma sample, then subsequent analysis of the spiked sample should yield 100% of the spiked amount of analyte within the error bounds of the assay, which are typically +/−5%.

For example, if 2 ug/mL of drug were spiked into a normal human sample, one would expect that between 1.90 ug/mL and 2.10 ug/mL would be found on subsequent analysis.

However, spiking a known amount of drug into a patient (or a sample therefrom) who had been injecting this drug subcutaneously for several months might give a recovery that is considerably less due to presence of ADAs.

Two or more spike and recovery points may enable the quantitative determination of the concentration of ADAs and their average affinity constant.

Interactions between binding proteins such as antibodies and their target analytes are governed by the Law of Mass Action (Eq 1)

$$K = C/(Ag)(Ab) \qquad 1.$$

Where C is the molar concentration of antibody-analyte complex, Ag is the concentration of free or unbound analyte and Ab is the concentration of antibody not bound in a complex with analyte.

This equation can be rewritten in terms of x which is the fraction of total analyte (Ago) bound in the complex $$C = xAgo \text{ where} \qquad 2.$$

$$Ag = (1-x)Ago \qquad 3.$$

$$Ab = Abo - xAgo \qquad 4.$$

Substituting produces Equation 5

$$K = xAgo/((1-x)Ago*(Abo-xAgo)) \qquad 5.$$

Which simplifies to Equation 6

$$K = x/(1-x)(Abo-xAgo) \qquad 6.$$

Multiplying through and transposing yields Equation 7

$$(1-x)*(Abo-xAgo) = x/K \qquad 7.$$

which can be further simplified to Equation 8

$$Abo - x(Ago+Abo) + x^2 Ago = x/K \qquad 8.$$

and in turn leads to Equation 9

$$X^2 Ago - x(Ago+Abo+1/K) + Abo = 0 \qquad 9.$$

On examination, Equation 9 is in the form of a quadratic equation and has the solution given in Equation 10

$$X=((b^2-4ac)^{1/2})/@=2a \qquad 10.$$

Where a=Ago, b=Ago+Abo+1/K and c=Abo

TABLE 2

For assumed values of K and Abo, the table shows the amounts of bound and free drug for various levels of total drug (Ago)

| ug/mL | [Drug]   | b        | X        | Bound Drug | Free Drug |
|-------|----------|----------|----------|------------|-----------|
| 0.05  | 3.33E−10 | 3.84E−07 | 8.69E−01 | 0.04       | 0.01      |
| 1     | 6.67E−09 | 3.90E−07 | 8.68E−01 | 0.87       | 0.13      |
| 2     | 1.33E−08 | 3.97E−07 | 8.66E−01 | 1.73       | 0.27      |
| 3     | 2.00E−08 | 4.03E−07 | 8.63E−01 | 2.59       | 0.41      |
| 5     | 3.33E−08 | 4.17E−07 | 8.59E−01 | 4.30       | 0.70      |
| 8     | 5.33E−08 | 4.37E−07 | 8.52E−01 | 6.82       | 1.18      |
| 12    | 8.00E−08 | 4.63E−07 | 8.42E−01 | 10.10      | 1.90      |
| 16    | 1.07E−07 | 4.90E−07 | 8.30E−01 | 13.29      | 2.71      |
| 32    | 2.13E−07 | 5.97E−07 | 7.71E−01 | 24.69      | 7.31      |
| K     | 2.00E+07 |          | 20       |            |           |
| Ab    | 3.33E−07 |          | 10       | 5 ug/mL    |           |

In the presence of antidrug antibodies, only the free drug is capable of being measured in the assay. Drug bound in an antidrug antibody complex cannot participate in another binding interaction due to steric hindrance.

In the situation where the total amount of drug is 8 ug/mL, the apparent amount of free drug would be measured as 1.18 ug/mL.

If we were to spike in an additional 4 ug/mL of drug, the total drug concentration would now be 12 ug/mL. But the observer who can only see free drug levels would detect only 1.90 ug/mL and not the 1.18 ug/mL plus the 4 ug/mL spike or 5.18 ug/mL. Only 36.6% of the expected drug level would be seen, as the vast majority of the drug both endogenous and spike is tied up in the antidrug complex.

Thereby, the method can be used to estimate the true level of ADAs in the sample.

The invention claimed is:

1. A method for determining the presence and quantity of one or more different TNF-α inhibitor drug antibodies in one or more biological samples each comprising less than 200μl, the method comprising the steps of:

a) providing a first TNF-α conjugate comprising TNF-α and a first conjugated moiety, b) providing a second TNF-α conjugate comprising TNF-α and a second conjugated moiety, said second moiety being capable of generating or ameliorating a detectable signal in the presence of a molecular complex comprising a TNF-α inhibitor and the first TNF-α conjugate and the second TNF-α conjugate, wherein the first and the second moieties are solid particles, further comprising adding a TNF-α inhibitor binding agent capable of ligating one TNF-α inhibitor with another TNF-α inhibitor or wherein the first moiety is an enzyme and the second moiety a substrate for the first moiety, or wherein the first moiety is an fluorophore and the second moiety a modulator of the fluorescence provided by the first moiety, c) providing a reaction liquid comprising the first and the second TNF-α conjugates and a spike containing a known amount of the TNF-α inhibitor, and contacting the sample with the reaction liquid, whereby a detection liquid comprising the sample potentially comprising the TNF-α inhibitor drug antibody, the spike amount of the TNF-α inhibitor and the first and the second TNF-α conjugates is formed, d) detecting the change in signal following step c, and e) determining the quantity of the TNF-α inhibitor by comparing the obtained results with an internal standard, and f) determining the presence or absence of the TNF-α inhibitor antibody by comparing the obtained results with an internal standard.

2. The method according to claim 1, comprising the performance of at least one repeat of steps a-f with a second spike of a known amount of the TNF-α inhibitor, or alternatively comprising the additional steps g and h of providing a second spike of a known amount of the TNF-a inhibitor, or adding the second spike to the detection liquid following step d, and, subsequently detecting the change in signal provided by the addition of the second spike, and determining the quantity of TNF-a inhibitor antibodies in the sample.

3. The method according to claim 1, wherein the TNF-α inhibitor is a prescription medicament.

4. The method according to claim 3, wherein the medicament is selected from the group consisting of etanercept, infliximab, adalimumab, certolizumab pegol, and golimumab.

5. The method according to claim 1, wherein the first moiety is Horseradish Peroxidase (HRP) and the second moiety is a substrate for HRP.

6. The method according to claim 1, wherein the first moiety is a fluorophore and the second moiety is a quencher.

7. The method of claim 6, wherein the fluorophore and quencher together comprise a system, wherein the system is a SPARCL (Spatial Proximity Analyte Reagent Capture Luminescence) system.

* * * * *